United States Patent
Lee et al.

(10) Patent No.: US 6,420,377 B1
(45) Date of Patent: *Jul. 16, 2002

(54) COVALENT CONJUGATES OF TOPOISOMERASE I AND TOPOISOMERASE II INHIBITORS

(75) Inventors: Kuo-Hsiung Lee, Chapel Hill, NC (US); Yung-Chi Cheng, Woodbridge, CT (US); Xin Guo, San Diego, CA (US); Kenneth F. Bastow, Chapel Hill; Hui-Kang Wang, Carrboro, both of NC (US)

(73) Assignees: The University of North Carolina at Chapel Hill, Chapel Hill, NC (US); Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/723,822

(22) Filed: Nov. 28, 2000

Related U.S. Application Data (63) Continuation of application No. 08/815,890, filed on Mar. 12, 1997.

(51) Int. Cl.⁷ ................... A61K 31/44; A61K 31/335
(52) U.S. Cl. ................ 514/280; 514/283; 514/285; 514/297; 514/463
(58) Field of Search ................ 514/280, 283, 514/285, 297, 463

(56) References Cited

U.S. PATENT DOCUMENTS

| | | | |
|---|---|---|---|
| 3,408,441 A | 10/1968 | von Wartburg et al. | 424/180 |
| 3,524,544 A | 8/1970 | Keller-Juslen | 260/210 |
| 4,197,246 A | 4/1980 | Murdoch et al. | 260/380 |
| 4,547,567 A | 10/1985 | Umezawa et al. | 536/17.2 |
| 4,564,675 A | 1/1986 | Kurabayashi et al. | 536/18.1 |
| 4,567,253 A | 1/1986 | Durst et al. | 536/18.1 |
| 4,716,221 A | 12/1987 | Umezawa et al. | 536/17.2 |
| 4,757,138 A | 7/1988 | Fujii et al. | 536/18.1 |
| 4,853,467 A | 8/1989 | Vyas et al. | 536/17.9 |
| 4,868,291 A | 9/1989 | Saulnier et al. | 536/18.1 |
| 4,874,851 A | 10/1989 | Vyas et al. | 536/17.2 |
| 4,888,419 A | 12/1989 | Saulnier et al. | 536/18.1 |
| 4,900,814 A | 2/1990 | Sterling et al. | 536/18.1 |
| 4,904,768 A | 2/1990 | Saulnier et al. | 536/17.1 |
| 4,912,204 A | 3/1990 | Ohnuma et al. | 536/18.1 |
| 4,916,217 A | 4/1990 | Saulnier | 536/17.1 |
| 4,935,504 A | 6/1990 | Saulnier et al. | 536/18.1 |
| 4,965,348 A | 10/1990 | Saulnier et al. | 536/17.2 |
| 4,997,931 A | 3/1991 | Ohnuma et al. | 514/27 |
| 5,034,380 A | 7/1991 | Ohnuma et al. | 514/27 |
| 5,061,791 A | 10/1991 | Showalter et al. | 536/17.4 |
| 5,064,823 A | 11/1991 | Lee et al. | 514/198 |
| 5,132,322 A | 7/1992 | Lee et al. | 514/468 |
| 5,206,350 A | 4/1993 | Wang et al. | 536/18.1 |
| 5,332,811 A | 7/1994 | Lee et al. | 544/148 |
| 5,459,248 A | 10/1995 | Silverberg et al. | 536/18.6 |
| 5,459,269 A | 10/1995 | Comins | 546/48 |
| 6,207,373 B1 * | 3/2001 | Lee | |

FOREIGN PATENT DOCUMENTS

| | | |
|---|---|---|
| CH | 0481097 | 12/1969 |
| CH | 0484101 | 2/1970 |
| EP | 111058 A | 11/1982 |
| EP | 0 321 122 A2 | 6/1989 |
| EP | 435709 A | 11/1989 |
| EP | 0 540 099 A1 | 5/1993 |
| GB | 1205966 | 9/1970 |
| JP | 5 8225096 A | 6/1982 |
| JP | 6 1134396 A | 12/1984 |
| WO | WO 94/11377 | 5/1994 |
| WO | WO 95/20567 | 8/1995 |
| WO | WO 96/23794 | 8/1996 |

OTHER PUBLICATIONS

CA 123:228772, Bosslet, 1995.*
CA 122:23317, Cortes, 1994.*
CA 81:45352, Kline, 1974.*
L. F. Liu, "DNA Topoisomerase Poisons as Antitumor Drugs," *Annu. Rev. Biochem.*, vol. 58, p. 351–375 (1989).
Bastow, K.F. et al., *Antitumor agents—CLXXIII. Synthesis and evaluation of camptothecin–4 beta–amino–4'–0–demethyl epipodophyllotoxin conjugates as inhibitors of mammalian DNA topoisomerases and as cytotoxic agents*, Bioorg Med. Chem, vol. 5(8), 1481–8 (Aug. 1997)(Abstract).
Poddevin B. et al., *Dual Topoisomerase I and II Inhibition by Introplicine (RP–60475), a New Antitumor Agent in Early Clinical Trials*, Molecular Pharmacology, 44(4), pp. 767–774 (1993).
Guo, X. et al., *Novel Biochemical and antitumor activity of the camptothecin–4 beta–amino–4'–0–demethyl epipodophyllotoxin conjugates* (meeting abstract), Proc. Annu. Meet., Am. Assoc. Cancer Res., 38, A4108 (1997).
Registry search report of RN 204133–84–6, 204133–83–5, and 204133–81–3, 1999.
CA 127:326521, 1997, Teicher.
CA 122:306028, Petersen, 1994.

* cited by examiner

*Primary Examiner*—D. Margaret Seaman
(74) *Attorney, Agent, or Firm*—Myers Bigel Sibley & Sajovec (57) ABSTRACT

The present invention provides covalent conjugates of topoisomerase I and topoisomerase II inhibitors. Such compounds have a structure according to formula I:

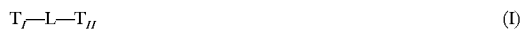

$$T_I{-}L{-}T_{II} \qquad (I)$$

wherein:

$T_I$ is a topoisomerase I inhibitor such as a camptothecin group;

$T_{II}$ is a topoisomerase II inhibitor such as an amsacrine, ellipticine, epipodophyllotoxin, or anthracycline antibiotic group; and L is a linking group.

The compounds are useful for inhibiting topoisomerase I and II enzymes, for promoting cellular differentiation, and for treating cancer.

8 Claims, 4 Drawing Sheets

K+/SDS-
Precipitable cpm.

COVALENT CONJUGATES OF TOPOISOMERASE I AND TOPOISOMERASE II INHIBITORS

This application is a continuation of Ser. No. 08/815,890, filed Mar. 12, 1997.

This Invention was made with Government support under Grant No. CA 17625 from the National Cancer Institute. The Government has certain rights to this invention.

FIELD OF THE INVENTION

The present invention concerns covalent conjugates of topoisomerase I inhibitors (e.g., camptothecins) and topoisomerase II inhibitors (e.g., amsacrine, ellipticines, anthracycline antibiotics, epipodophyllotoxins).

BACKGROUND OF THE INVENTION

Etoposide is a widely-used antineoplastic agent which inhibits mammalian DNA topoisomerase II isoenzymes. See, F. Drake et al., *Biochem.* 28:8154 (1989); P. Watt and I. Hickson, *Biochem. J.* 303:681 (1994); and Y. Pommier, *Cancer Chemo. & Pharmac.* 32:103 (1993). Various etoposide derivatives have been developed in order to improve antitumor activity, cytotoxicity against drug resistant cells and drug-formulation characteristics including the 4'-O-demethylepipodophyllotoxins bearing C-4β-N-linked substituents. See, Y. Zhang and K. H. Lee, *Chin. Pharm. J.*, 46:319 (1994). The other mammalian DNA topoisomerase, a type I enzyme, is also considered to be a useful therapeutic target. Several selective inhibitors have been identified to date including the antitumor alkaloid, camptothecin, (CPT) and two analogs are currently approved for clinical use in the United States. See, P. Watt and I. Hickson, *Biochem. J.* 303:681 (1994); and A. Chen and L. Liu, *Annu. Rev. Pharmacol. Toxicol.* 34:191 (1994). However, not all topoisomerase inhibitors of potential clinical value are topoisomerase-type specific. For example, a 7-H-benzopyrido (4,3-b) indole-derivative (inotoplicine), inhibits topoisomerases I and II simultaneously and can circumvent topoisomerase-mediated mechanisms of drug-resistance. See, B. Podderin et al., *Mol. Pharmacol.* 44:767 (1993).

All of the above-mentioned compounds share a common inhibitory mechanism which is understood in some depth at the biochemical level. Enzyme inhibition involves the trapping of a putative covalent reaction intermediate called a reversible "cleavable complex". The intracellular lesion, presumably a topoisomerase-DNA-drug ternary complex, ultimately leads to cell death. Although the cytotoxic events depend on the particular type of topoisomerase involved, the precise biochemical pathway(s) to cell killing remains to be defined. See, P. Watt and I. Hickson, *Biochem. J.* 303:681 (1994); A. Chen and L. Liu, *Annu. Rev. Pharmacol. Toxicol.* 34:191 (1994); and P. Darpa et al., *Cancer Res.* 50:6919 (1990).

SUMMARY OF THE INVENTION

A first aspect of the present invention is covalent conjugates of topoisomerase I and topoisomerase II inhibitors. Such compounds have a structure according to formula I:

wherein:

$T_I$ is a topoisomerase I inhibitor such as a camptothecin group;

$T_{II}$ is a topoisomerase II inhibitor such as an amsacrine, ellipticine, epipodophyllotoxin, anthracycline antibiotic group, or mitoxantrone group; and L is a linking group.

The compounds of formula I are useful as, among other things, inhibitors of topoisomerase I and topoisomerase II.

The present invention is explained in greater detail in the drawings herein and the specification set forth below.

BRIEF DESCRIPTION OF THE DRAWINGS

FIG. 3. Reversible genomic DNA fragmentation detected by a gel lysis assay method. KB cells were immobilized in agarose plugs, lysed and analyzed as described in "Material and Methods". Cells were prepared immediately following three hours of treatment (lanes 3, 5, 7, 8, 10 and 11) or following an additional hour of incubation in fresh growth medium lanes 4, 6, 9 and 12). Treatments are indicated under the sample lanes and concentrations used are given in the text under "Results". The first two lanes are control samples from KB cells mock-treated with 0.5% (v/v) dimethylsulfoxide as a carrier control; lane 1 is DNA from cells treated for three hours and the other sample was prepared following a one hour treatment reversal. Arrows in the left margin indicate the plug position at the gel origin and the mobility of phage lambda DNA molecular mass markers in Kb.

FIGS. 4A and 4B. In vivo effects of compounds S-1 and S-2 in nude mice with KB cell tumor development. In FIG. 4A: control (-●-), etoposide C-1 (. . . Δ . . . ), camptothecin C-2 (--○--), S-1 at 3 mg/kg/day (--■--), S-1 at 7.5 mg/kg/day (--▲--), and S-1 at 15 mg/kg/day (-·▼-·). In FIG. 4B: control (-●-), etoposide C-1 (. . . Δ . . . ), camptothecin C-2 (--○--), S-2 at 15 mg/kg/day (--▽--), and S-2 at 50 mg/kg/day (--○--).

DETAILED DESCRIPTION OF THE INVENTION

As used herein the term "alkyl" refers to $C_{1-20}$ inclusive, linear, branched, or cyclic, saturated or unsaturated hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, and allenyl groups. Thus, the term "alkyl" refers to $C_{1-20}$ inclusive alkyls unless otherwise specified. The term "alkylene" refers to $C_{1-20}$ inclusive alkyls. The term "alkenyl" refers to $C_{1-20}$ inclusive alkyls containing one or more double bonds. The term "alkoxy" as used herein refers to $C_{1-20}$ inclusive, linear, branched, or cyclic, saturated or unsaturated oxo-hydrocarbon chains, including for example methoxy, ethoxy, propoxy, isopropoxy, butoxy, t-butoxy, and pentoxy. The term "aryloxyl" as used herein refers to phenyloxyl and alkyl or alkoxyl substituted phenyloxyl. The term "arylene" as used herein refers to phenylene and alkyl or alkoxyl substituted phenylene. The terms "halo," "halide," or "halogen" as used herein refer to fluorine, chlorine, bromine, and iodine.

As noted above, the present invention is concerned with compounds that are active as topoisomerase I and topoisomerase II inhibitors. Such compounds have a structure according to formula I:

$$T_I—L—T_{II} \qquad (I)$$

wherein $T_I$ is a topoisomerase I inhibitor, $T_{II}$ is a topoisomerase II inhibitor, and L is a covalent linking group. As will be appreciated by those skilled in the art, the topoisomerase I inhibitor may be either a selective topoisomerase I inhibitor (that is, have essentially no topoisomerase II inhibitory activity; for example, a camptothecin group) or may be a mixed inhibitor (that is, have both topoisomerase I and topoisomerase II inhibitory activity). Likewise, the topoisomerase II inhibitor may be either a selective topoisomerase II inhibitor (that is, have essentially no topoisomerase I inhibitory activity; for example, an amsacrine, ellipticine, epipodophyllotoxin, anthracycline antibiotic group or mitoxantrone) or may be a mixed inhibitor. Preferably, at least one of the topoisomerase I and topoisomerase II inhibitors is a selective inhibitor, and more preferably both of the topoisomerase I and topoisomerase II inhibitors are selective inhibitors.

A. Topoisomerase I Inhibitors

Particularly preferred topoisomerase I inhibitors are camptothecin groups (the term "camptothecin group" is intended to encompass camptothecin and analogs thereof). Such compounds are typically of the formula II:

wherein:
  $R_1$ is selected from the group consisting of H, alkyl, alkoxy, alkylaryl, hydroxyalkyl, haloalkyl, aminoalkyl, dialkylamino, dialkylaminoalkyl, cycloaminoalkyl, aryl, aryloxy, C-glycal, $CO_2R_7$, nitro, cyano, halo, $SR_8$, $NR_8R_8$, O-glycosyl and L-$T_{II}$; and
  $R_2$, $R_3$, R4 and $R_5$ are each independently H, amino, hydroxy, alkyl, alkoxy, alkylthiol, alkylamino, aminoalkyl, di(alkyl)amino, cycloaminoalkyl, aminoalkoxy, aryl, aryloxy, C-glycal, cyano, methylenedioxy, formyl, nitro, halo, trifluoromethyl, aminomethyl, azido, amido, hydrazino, any of the twenty standard amino acids bonded to the A ring via the amino-nitogen atom, $SR_8$, $NR_{88}$, or O-glycosyl, L—$T_{II}$; or $R_3$ and $R_4$ together form a 5- or 6-member aromatic or dioxolane ring; and wherein methylenedioxy comprises $R_2$ and $R_3$, $R_3$ and $R_4$, or $R_4$ and $R_5$ taken together;

$R_7$ is ethyl; and each $R_8$ is independently selected from the group consisting of H, alkyl, alkylaryl, hydroxyalkyl, aminoalkyl, acyl, or aryl;

subject to the proviso that one of $R_1$, $R_2$, $R_3$, $R_4$, and $R_5$ is a substituent of the formula —L—$T_{II}$, wherein L is a covalent linking group; and $T_{II}$ is a topoisomerase II inhibitor.

Substituents on the "A" ring of the compounds of formula II may be joined together to form a bifunctional substituent such as the methylenedioxy group. Methylenedioxy substituents may be bonded to any two consecutive positions in the A ring, for example, the 9,10, the 10,11, or the 11,12 positions.

Substituents which are standard amino acids may be any of the twenty amino acids commonly found in naturally occurring proteins, and are well known in the art. These provide a substituent of the formula —NHCHRCOOH, with R being the side chain of any of the twenty standard amino acids. The amino acids may be of any configuration, but preferably have an (L) configuration.

B. Topoisomerase II Inhibitors $T_{II}$ is a topoisomerase II inihibitor. Suitable topoisomerase II inhibitor groups include groups which inhibit both topoisomerase I and topoisomerase II as well as groups which inhibit topoisomerase II selectively. As will be apparent to those skilled in the art, the conjugates of the present invention are comprised of one group, which alone is a topoisomerase I inhibitor, and one group, which alone is a topoisomerase II inhibitor, and a linking group which joins the foregoing groups to form the conjugate. Accordingly by the statement that the $T_{II}$ group is a topoisomerase II inhibitor is meant that $T_{II}$ is a group derived from and based upon a parent compound which exhibits topoisomerase II inhibition activity. Accordingly, there are a number of topoisomerase II inhibitor compounds from which the topoisomerase II inhibiting group $T_{II}$ may be drawn, which compounds are well known to those skilled in the art. For example, suitable topoisomerase II inhibiting compounds are those compounds within the general classes of epipodophyllotoxins, amsacrines, ellipticines, anthracycline antibiotics, and mitoxantrones.

1. Epipodophyllotoxin Groups

One suitable class of compounds within the scope of the definition of $T_{II}$ is the epipodophyllotoxin class of compounds. Suitable topoisomerase II inhibiting groups derived from the epipodophylotoxin class of compounds include groups of the general formula III-A:

III-A wherein $R_{10}$, $R_{11}$, $R_{12}$, and $R_{16}$ are each independently selected from the group consisting of H and halo; $R_{13}$ and $R_{15}$ are each independently alkoxy; and $R_{14}$ is selected from the group consisting of H, hydroxyl, alkyl, and phosphate salt. As will be apparent to the skilled artisan, the unoccupied bond represents the location at which this particular $T_{II}$ group is joined to the linking group L.

Specific examples of preferred $T_{II}$ groups of formula III-A include groups wherein $R_{10}$, $R_{11}$, $R_{12}$, and $R_{16}$ are each H; groups wherein $R_{13}$ and $R_{15}$ are each methoxy; and groups wherein $R_{14}$ is hydroxyl.

Specific examples of topoisomerase II inhibiting compounds from which the $T_{II}$ group may be derived include but are not limited to etoposide and teniposide.

2. Amsacrine Groups

Another suitable class of compounds within the scope of the definition of $T_{II}$ is the amsacrine class of compounds. Suitable topoisomerase II inhibiting groups derived from the amsacrine class of compounds include groups of the general formula III-B:

III-B wherein $R_{20}$ and $R_{21}$ are independently selected from the group consisting of alkoxy and alkylhydroxyl. As will be apparent to the skilled artisan, the unoccupied bond represents the location at which this particular $T_{II}$ group is joined to the linking group L.

Specific examples of preferred $T_{II}$ groups of formula III-B include those compounds wherein $R_{20}$ is methoxy; and groups wherein $R_{21}$ is —$CH_2OH$.

Specific examples of topoisomerase II inhibiting compounds from which the $T_{II}$ group may be derived include but are not limited to m-AMSA.

3. Ellipticine Groups

Another suitable class of compounds within the scope of the definition of $T_{II}$ is the ellipticine class of compounds. Suitable topoisomerase II inhibiting groups derived from the ellipticine class of compounds include groups of the general formula III-C:

III-C wherein $R_{30}$ is H or aliphatic amine; $R_{31}$ is H or —C(O)—N($R_{35}$)—$(CH_2)_n$—N($R_{36}$)($R_{37}$) wherein $R_{35}$, $R_{36}$, and $R_{37}$ are each independently selected from the group consisting of H and alkyl and n is an integer from 1 to 6; $R_{32}$ and $R_{34}$ are each indepently selected from the group consisting of H and alkyl; and $R_{33}$ is alkyl. As will be apparent to the skilled artisan, the unoccupied bond represents the location at which this particular $T_{II}$ group is joined to the linking group L.

Specific examples of preferred $T_{II}$ groups of formula III-C include those groups wherein $R_{30}$ is H; groups wherein $R_{30}$ is an aliphatic amine particularly, propylamine and N-diethylpropylamine; groups wherein $R_{31}$ is H; groups wherein $R_{32}$ is alkyl, particularly methyl; groups wherein $R_{33}$ is methyl; and groups wherein $R_{34}$ is H.

Specific examples of topoisomerase II inhibting compounds from which the $T_{II}$ group may be derived include but are not limited to ellipticine.

4. Anthracycline Antibiotic Groups

Another suitable class of compounds within the scope of the definition of $T_{II}$ is the anthracycline antiobiotic class of compounds. Suitable topoisomerase II inhibiting groups derived from the anthracycline antibiotic class of compounds include groups of the general formula III-D:

III-D wherein $R_{40}$ is H or alkoxy; $R_{41}$ is hydroxyl or O—; $R_{42}$ is alkylhydroxyl, or $CH_2O$—; and $R_{43}$ and $R_{44}$ are each independently selected from the group consisting of H and hydroxyl; subject to the provisos that if $R_{41}$ is hydroxyl, then $R_{42}$ is $CH_2O$—; and if $R_{42}$ is alkyl or alkylhydroxyl, then $R_{41}$ is O—. As is apparent to those skilled in the art, the unoccupied bond (i.e., O— or $CH_2O$—) represents the location at which this particular $T_{II}$ group is joined to the linking group L.

Specific examples of preferred $T_{II}$ groups of formula III-D include those groups wherein $R_{40}$ is alkoxy, particularly methoxy; groups wherein $R_{41}$ is hydroxyl; groups wherein $R_{41}$ is O—; groups wherein $R_{42}$ alkylhydroxyl; groups wherein $R_{42}$ is $CH_2O$—; groups wherein $R_{43}$ is H and R44 is hydroxyl. As will be clear to those skilled in the art, at least one of $R_{41}$ and $R_{42}$ must possess the bond joining the $T_{II}$ group to L. Hence, if $R_{41}$ is not O—, then $R_{42}$ must be $CH_2O$—. $R_{41}$ must not be O— if $R_{42}$ is $CH_2O$—.

Specific examples of topoisomerase II inhibting compounds from which the $T_{II}$ group may be derived include but are not limited to adriomycin, doxorubicin, daunorubicin, epirubicin, and idarubicin.

5. Mitoxantrone Groups

Another suitable class of compounds within the scope of the definition of $T_{II}$ is the mitoxantrone class of compounds. Suitable topoisomerase II inhibiting groups derived from the mitoxantrone class of compounds include groups of the general formula III-E:

III-E wherein $R_{50}$, $R_{51}$, $R_{52}$ and $R_{53}$ are each independently selected from the group consisting of OH or O—; subject to the proviso that one of $R_{50}$, $R_{51}$, $R_{52}$ and $R_{53}$ is O—. As is apparent to those skilled in the art, the unoccupied bond (i.e., O—) represents the location at which this particular $T_{II}$ group is joined to the linking group L.

Specific examples of preferred $T_{II}$ groups of formula III-E include those groups wherein $R_{52}$ is O—; and compounds wherein $R_{50}$ is O—.

Specific examples of topoisomerase II inhibting compounds from which the $T_{II}$ group may be derived include but are not limited to mitoxantrone.

C. Linking Groups

The specific linking group employed will depend upon the particular synthetic method used to make the covalent conjugate, as will be appreciated by those skilled in the art. The linking group "L" may be considered as a separate group, as in formula I above, or may be considered as a side-chain of either (or both) of the topoisomerase I and the topoisomerase II inhibitor.

Many suitable linking groups will be determinable by those skilled in the art. A suitable linking group will permit the joining of the topoisomerase I (i.e., $T_I$) and topoisomerase II ($T_{II}$) inhibitors to provide a metabolically stable conjugate (i.e., a conjugate for which steric hinderance will not be so strong as to prevent the joining of the $T_I$ and $T_{II}$ groups).

Specific examples of suitable linking groups within the scope of the definition of L include but are not limited to:

wherein a is a 0–3; b is a 0–3; and $R_{70}$ is selected from the group consisting of alkylene, alkenyl, and arylenyl.

D. Example Compounds

Specific examples of compounds within the scope of the present invention include but are not limited to:

S-1

-continued

S-2

E. Synthesis of Compounds

A wide variety of the topoisomerase I and topoisomerase II inhibiting conjugates of the present invention can be prepared according to the following general techniques. Variations on the following general synthetic method will be readily apparent to those skilled in the art and are deemed to be within the scope of the present invention. In general, the conjugates of formula I may be prepared by refluxing a topoisomerase I inhibitor compound with a topoisomerase II inhibitor compound in tetrahydrofuran.

As a specific example, the conjugates S-1 and S-2 above may be prepared by dissolving 7-formyl camptothecin and 4-demethylepipodophyllotoxin derivatives in dry tetrahydrofuran. Then 1.0 M hydrogen chloride ether solution is added to adjust the pH to 1–2. The solution is refluxed for 1 hour and evaporated to dryness. The reaction produces the compounds in 70–80% yield. As will be apparent to those skilled in the art, the structures of the conjugates produced may be determined using conventional spectroscopic and analytical techniques.

F. Pharmaceutical Formulations

The topoisomerase I and topoisomerase II inhibiting compounds of formula I of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of Formula I may be formulated for administration for the treatment of a variety of conditions. In the manufacture of a pharmaceutical formulation according to the invention, the compounds of Formula I and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3(6):318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

G. Utilities and Methods of Use

In addition to the compounds of formula I, the present invention also provide useful therapeutic methods. For example, the present invention also provide a method of inhibiting topoisomerase I and topoisomerase II enzymes. The method includes contacting topoisomerase I and topoisomerase II in vitro or in vivo with an inhibitory effective amount of a compound of formula I. The inhibition of topoisomerase I and II is a useful means of inhibiting cancer cell growth.

The present invention also provides a method of inducing cellular differentiation. The method includes contacting a cancer cell with a differentiation effective amount of a compound of formula I. Cancer cells which may be differentiated include cells from small cell lung cancer, testicular cancer, lymphoma, leukemia, esophageal cancer, stomach cancer, colon cancer, breast cancer, central nervous system cancer, liver cancer and prostate cancer.

The present invention also provides a method of treating cancer in a subject afflicted with cancer. The method includes administering to the subject in an effective cancer treating amount a compound of formula I. The methods are useful for the treatment of a variety of cancer cells which include but are not limited to small cell lung cancer, testicular cancer, lymphoma, leukemia, esophageal cancer, stomach cancer, colon cancer, breast cancer, central nervous system cancer, liver cancer and prostate cancer.

Subjects which may be treated using the methods of the present invention are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the compounds of Formula I, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting examples, wherein the following abbreviations are used: "THF" means tetrahydrofuran; "SDS" means sodium dodecylsulfate; "PBS" means 140 mM NaCl, 4 mM KCl, 0.5 mM $Na_2HPO_4$, 150 mM $KH_2PO_4$; "TBE" means 95 mM tris-borate, 2 mM EDTA pH 8; "mAMSA" means 4'-(9-acridinylamino)-methanesulfon-m-anisidide; "EDTA" means disodium(ethylenedinitrilo) tetraacetic acid; "RN'ase" means bovine pancreatic ribonuclease; and "PFGE" means pulsed-field gel electrophoresis.

EXAMPLE 1

Conjugate Synthesis

Compounds S-1 and S-2 were synthesized according to the procedure shown in the following Scheme 1:

4a: R' = p-$NH_2$•HCl
4b: R' = o-$NH_2$•HCl

In general, 7-formyl camptothecin (1 eq.) and 4-demethylepipodophyllotoxin derivatives (4a or 4b, 1 eq.) were dissolved in dry THF, and 1.0 M hydrogen chloride ether solution was added to adjust the pH to 1–2. The solution was refluxed for 1 hour and evaporated to dryness. The residue was purified via column chromatography (silica gel with chloroform methanol, 100:1 (v/v) as the eluent) to give target compounds in 70–80% yield. The structures of final products were secured by spectroscopic and analytical data.

Compound S-1, red crystals, mp>300° C. (decomp.), IR (KBr) $cm^{-1}$ 3350 (broad, OH, NH), 1770 (sh., δ-lactone), 1650 (carbonyl of amide); $^1$H NMR ($CDCl_3$) 67 : 1.06 (t, J=7.5 Hz, 3H, 18'''-H), 1.97 (q, J=7.5 Hz, 2H, 19'''-H), 3.14 (m, 1H, 3-H), 3.28 (dd, J=4.9, 14.0 Hz, 1H, 2-H), 3.80 (s, 6H, $OCH_3$×2), 4.05, 4.48 (t, J=8.7 Hz, 1H each, 11-H), 4.62 (d, J=4.9 Hz, 1H, 1-H), 4.86 (d, J=3.9 Hz, 1H, 4-H), 5.35, 5.69 (ABq, J=16.0 Hz, 1H each, 17'''-H), 5.72 (s, 2H, 5'''-H), 5.97 (d, J=5.1 Hz, 2H, $OCH_2Q$), 6.36 (s, 2H, 2', 6'-H), 6.54 (s, 1H, 8-H), 6.76 (d, J=8.7 Hz, 2H, 2", 6"-H), 6.85 (s, 1H, 5-H), 7.56 (d, J=8.7 Hz, 2H, 3", 5"-H), 7.76 (s, 1H, 13'''-H), 7.79, 7.89 (t, J=8.0 Hz, 1H each, 10''', 11'''-H), 8.25, 8.61 (d, J=8.0 Hz, 1H each, 9''', 12'''-H), 9.60 (s, 1H, N=CH); Anal. Calcd. for $C_{48}H_{40}N_4O_{11}$·$H_2O$: C 66.50, H 4.88, N 6.46; Found C 66.81, H 4.90, N 6.50.

Compound S-2, red crystals, mp 255–256° C. (decomp.), IR (KBr) $cm^{-1}$ 3350 (broad, OH, NH), 1770 (sh., β-lactone), 1650 (carbonyl of amide); $^1$H NMR ($CDCl_3$) δ: 1.05 (t, J=7.5 Hz, 3H, 18'''-H), 1.91 (m, 2H, 19'''-H), 3.10 (m, 1H, 3-H), 3.37 (dd, J=4.9, 14.2 Hz, 1H, 2-H), 3.81 (s, 6H, $OCH_3$×2), 4.08 (dd, J=2.9, 8.0 Hz, 1H, 11-H), 4.46 (t, J=8.0

Hz, 1H, 11-H), 4.74 (d, J=4.9 Hz, 1H, 1-H), 4.84 (t-like, 1H, 4-H), 5.28 (s, 1H, 2"-H), 5.23, 5.42 (ABq, J=20.5 Hz, 1H each, 17'''-H), 5.30, 5.74 (ABq, J=16.6 Hz, 1H each,, 5'''-H), 5.96 (d, J=5.5 Hz, 2H, $OCH_2O$), 6.37 (s, 2H, 2', 6'-H), 6.49 (s, 1H, 8-H), 6.71, 6.90 (both d, J=7.5 Hz, 1H each, 2", 5"-H), 6.86 (s, 1H, 5-H), 7.33, 7.35 (t, J=7.5 Hz, 1H, 3", 4"-H), 7.62 (s, 1H, 13'''-H), 7.71, 7.87 (t, J=8.0 Hz, 1H each, 10''', 11'''-H), 8.28, 8.57 (d, J=8.0 Hz, 1H each, 9''', 12'''-H), 9.55 (s, 1H, N=CH); Calcd. for $C_{48}H_{40}N_4O_{11}\cdot 0.5H_2O$: C 67.18, H 4.82, N 6.53; Found C 67.04, H 4.88, N 6.41.

EXAMPLE 2

Enzymes and Reagents

Calf thymus DNA topoisomerases were purchased from TopoGen Inc., Columbus, Ohio. Tritium-labeled thymidine (60–90 ci/mmol) for labeling cellular DNA to measure protein-DNA complexes and $\alpha P^{32}$-labeled deoxycytidine triphosphate (>3000 ci/mmol) were obtained from ICN Biochemicals Inc., Irvine, Calif. The latter radiochemical was used with a T4-DNA polymerase polymerase-labeling system from BRL Inc., Gaithersburg, Md., to prepare $P^{32}$-plasmid DNA for in vitro cleavage assays. Tissue culture reagents were purchased from Sigma Chemical Co., St. Louis, Mo., and Gibco-BRL Inc. All other chemicals were reagent grade.

EXAMPLE 3

Drugs

Etoposide and camptothecin were obtained from the Natural Products Laboratory, UNC-Chapel Hill. The derivatives 3, 4a and 4b were prepared according to published methods described in H. K. Wang et al., *Bioorg. & Med. Chem.* 2:1397 (1994) and Z. Q. Wang et al., *J. Med. Chem.* 33:2660 (1990). All compounds were dissolved to 20 mM final concentration in dimethylsulfoxide and stored at minus 70° C. Immediately before use, compounds were diluted in water for biochemical studies or in culture medium under sterile conditions for cell-based assays.

EXAMPLE 4

Cell Lines and Cultures

The KB oral carcinoma cell line was provided by M. Fisher (Pharmacology, UNC- Chapel Hill). The isolation and properties of the etoposide-resistant sub-clone, KB-7d, and the camptothecin-resistant line, KB-CPT100, were reported in P. Ferguson et al., *Cancer Res.* 48:5956 (1988) and D. Beidler et al., *Cancer Res.* 56:345 (1996), and are discussed briefly hereinafter. The vincristine-resistant sub-clone, KB-VIN20c was isolated by selection in 20 nM vincristine and over-expresses the P-glycoprotein multidrug-resistant drug-efflux protein (unpublished results).

All cell types were propagated in RPMI-1640 medium supplemented with 5% (v/v) fetal calf serum and 100 μg/mL kanamycin at 37° in a humidified atmosphere of 5% $CO_2$ and 95% air. Over the course of the experiments, doubling times of cells were 24±4 hours.

Fifty thousand cells were plated in 25 cm² flasks (Falcon, N.J., USA) and incubated overnight. The medium was supplemented with test compounds at various concentrations and cultures were incubated for 48–51 hours (for about two cell doublings) before cells were trypsinized and then counted using a hemacytometer. The number of treated cells which excluded 0.5% (v/v) trypan blue were expressed as a percentage of the growth measured in control cultures. Compounds were evaluated in at least two independent experiments and the combined results were analyzed as scatter plots with dose-responses being computer fitted by linear regression at the 95% confidence level using Graphpad Software., San Diego, Calif. The $IC_{50}$ concentrations which inhibited cell growth by fifty percent relative to control were interpolated from graphed results.

EXAMPLE 5

Cytotoxicity Assay $LC_{50}$ concentrations were determined by treating cells for three hours with different concentrations of compounds then replating cells to measure colony formation and plating efficiency as the percent of total cells forming colonies. Compounds were evaluated in three independent experiments. The plating efficiencies of untreated cells varied between experiments with values ranging from 14–31% for KB, 31–56% for KB-7d, 16–38% for KB-VIN20c and 21–36% for KB-CPT100. A concentration of compound that reduced plating efficiency by fifty percent relative to control, the $LC_{50}$, was determined graphically as stated in the preceding section.

EXAMPLE 6

Cellular Protein-DNA Complex Formation

Stimulation of intracellular protein associated DNA breaks was measured using a standard assay method described in Y. Kashiwada et al., *J. Pharm. Sci.* 82:487 (1993). Briefly, KB cells were labeled overnight with tritiated thymidine (0.5 μCi/mL), chased for two hours and then treated in triplicate with test compounds at various concentrations. After one hour, samples were processed and protein-DNA complexes were measured as potassium-SDS precipitable radioactivity.

EXAMPLE 7

In Vitro Topoisomerase-DNA Cleavage Assay

The detailed method used to measure stimulation of cleavable complexes in vitro is described in K. Bastow et al., *Planta Med.* 59:195 (1993).. Briefly, incubated cleavage reactions containing one nanogram of $P^{32}$ end-labeled linearized PBR322 DNA, one unit of enzyme and test compound were divided equally for analysis. One portion was prepared for gel electrophoresis with subsequent autoradiography and protein-DNA complexes in the remaining sample were analyzed using the potassium-SDS precipitation method and scintillation spectrometry.

EXAMPLE 8

Gel Lysis Assay Method for DNA Breaks

The procedure used to detect inhibitor-induced cleavable-complexes as genomic DNA fragmentation on agarose gels is based on the procedure described in P. Walker et al., *Biotechniques* 15:1032 (1993), with suggested modifications (Goz B, LaBiche R; personal communication) as follows. One million KB cells in 25cm² flasks were treated for three hours with test compound, the medium was discarded then cells were scraped into ice-cold PBS and harvested by centrifugation. Washed cell pellets were resuspended in eighty microliters of a 37° C. gel solution [1%

(w/v) low-melting point agarose in PBS], and were cast in a mold and refrigerated to form 6×7×2 mm agarose plugs. Plugs of cells were incubated in lysis-digestion buffer (0.4M EDTA, 0.01 Tris (HCl, pH 8.0), 1% (w/v) N-lauryl-sarcosine and 100 µg/mL proteinase K) at 37° overnight or 50° for one hour. The treated plugs were equilibrated in TBE buffer and placed against a gel comb in a horizontal gel casting tray (BRL Inc., H4 system format). A 55° gel solution containing 0.8% (w/v) agarose in TBE was poured and allowed to gel. Electrophoresis was at 3.5 v/cm (measured between electrodes) for 16 hours at 4° without buffer re-circulation. The gel was stained with 1 µg/mL ethidium bromide in water, treated overnight at 25° C. with RN'ase (1 µg/mL), and then photographed under UV illumination. For the reversibility studies, treated cells were washed with PBS and incubated with fresh media for an additional hour before harvesting for plug preparation and gel analysis.

EXAMPLE 9

Stimulation of In Vitro Cleavable-Complexes by Conjugated Inhibitors

Figure 1A:
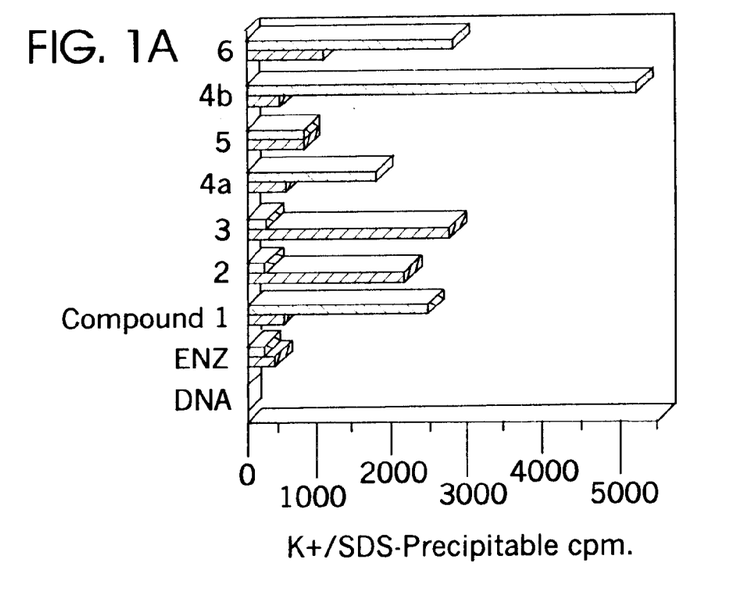
FIGS. 1A and 1B. Topoisomerase-DNA complex formation in vitro. A. Potassium-SDS precipitable radioactivity recovered from cleavage reactions containing topoisomerase I (stippled boxes) and topoisomerase II (shaded boxes), alone or with compounds 1–6 at ten micromolar. Input radioactivity was about 7000 $P^{32}$ cpm. Data are single determinations from the same experiment. B. Agarose gel autoradiogram of topoisomerase II-induced DNA cleavage products. Treatment conditions are indicated above the lanes and potassium-SDS precipitable radioactivity recovered are given below. Input radioactivity was about 5000 $P^{32}$ cpm. DNA fragments discussed in the text are indicated by small open circles in the right margin of lane 7. Non-adjacent lanes from a single gel autoradiogram were juxtaposed to prepare this figure.

Compounds were evaluated as cleavable complex-forming inhibitors of calf thymus DNA topoisomerases I and II in vitro. The prototypical inhibitors etoposide (C-1) and camptothecin (C-2) were included as reference standards. Activities and specificities of compounds tested at ten micromolar are depicted in FIG. 1A. The enzyme specificity and activity of three unconjugated inhibitors were consistent with measurements made using human enzymes and cellular assay systems as described in H. K. Wang et al., *Bioorg. & Med. Chem.* 2:1397 (1994) and Z. Q. Wang et al., *J. Med. Chem.* 33:2660 (1990). In contrast, compound 4a was less active than 1 at stimulating topoisomerase II-mediated DNA cleavage in vitro and not three fold more active based on an earlier study with a cell-based assay system reported in Z. Q. Wang et al., *J. Med. Chem.* 33:2660 (1990). Compound 4b has not been evaluated previously but it displayed similar properties as the meta-substituted congener. The conjugated inhibitors, S-1 and S-2, induced cleavable complexes with both types of enzyme however, their activities were reduced about two-fold relative to the unconjugated components 3, 4a and 3, 4b respectively. Results are reported in FIG. 1A.

Figure 1B:
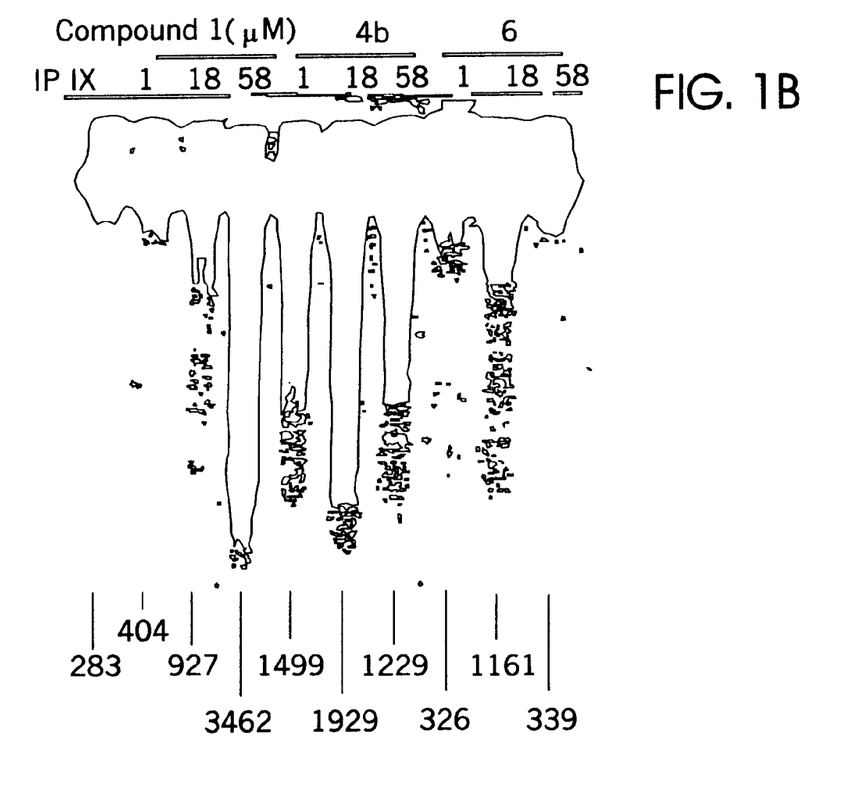

These results indicate that S-1 and S-2 displayed the combined selectivity of the unconjugated inhibitors but had lower relative activities at the single concentration tested. Compound S-2 was selected for further evaluation since the levels of S-2-induced and etoposide-induced DNA cleavage were similar. Concentration-dependent in vitro cleavage results using topoisomerase II as well as gel analysis of cleavage products are shown in FIG. 1B. Etoposide (C-1), stimulated enzyme induced cleavage 1.5-, 3, and 12-fold at one, ten and fifty micromolar respectively. A different activity profile was displayed by compounds 4b and S-2 in that induced levels of cleavage were maximal at ten micromolar, being about 7- and 4-fold increased over enzyme controls respectively. Compound 4b was about four times more active than C-1 at one micromolar and three-times less active at fifty micromolar. For similar treatments with compound S-2, only marginal stimulation of enzyme-mediated DNA cleavage was detected. Interestingly, some enzyme cleavage sites induced by compounds 4b and etoposide were also distinguishable because at least two unique cleavage fragments were produced upon 4b-treatment. Similar fragments were faintly visible as cleavage products induced by ten micromolar treatment with S-2. These results are reported in FIG. 1B. Additional studies with topoisomerase I showed that the stimulation of cleavage activity by both 3 and S-2 was not inhibited at higher test concentrations, however, the alkaline-treated reaction products were too numerous and heterogeneously-sized on autoradiographs to allow meaningful comparisons of cleavage site-specificies. Based on the overall findings, activity as cleavable complex-forming inhibitors was reduced by conjugation yet specific interactions in the presumed ternary complexes appeared to be unaffected.

EXAMPLE 10

Cell Growth Inhibition by a Conjugated Inhibitor

Compounds 3, 4b and S-2 were evaluated as cell growth inhibitors of KB, KB-7d, KB-CPT100, and KB-VIN20c and $IC_{50}$ values were established. The -7d cell line is a pleiotrophic multidrug resistant KB-subclone which exhibits 145-fold resistance to etoposide ($IC_{50}$ for KB, 0.16±0.04 micromolar), in part because of reductions in both drug uptake and intracellular levels of topoisomerase II. Furthermore, KB-7d cells are cross-resistant to structurally diverse topoisomerase II-targeting drugs including doxorubicin, mAMSA and mitoxantrone but are not cross-resistant to 10-hydroxy-camptothecin, a camptothecin analog described in P. Ferguson et al., *Cancer Res.* 48:5956 (1988). The -CPT100 cell line exhibits a 32-fold resistance to the growth-inhibitory effect of ($IC_{50}$ for KB, 9.8±3.2 nM) and a reduced intercellular level, about two-fold, of topoisomerase I; these cells are not cross-resistant to C-1. The resistance phenotype of -CPT100 cells appears to be independent of topoisomerase I but the biochemical mechanism remains to be fully characterized. Results from growth inhibition assays are given in Table 1.

TABLE 1

| | Cell Growth Inhibition | | |
| --- | --- | --- | --- |
| | $IC_{50}$ (nM) | | |
| Cell line | S-2 | 3 | 4b |
| KB | 14 (10, 18) | 7 (5, 9) | 100 (72, 128) |
| KB-7d | 15 (11, 19) | 9 (5, 13) | 388 (306, 460) |
| KB-CPT100 | 85 (71, 99) | 575 (435, 705) | 134 (112, 156) |
| XB-VIN20c | 27 (21, 33) | 18 (14, 22) | 234 (144, 309) |

Compound 4b was about 1.5-fold more active than C-1 at inhibiting KB cell growth with an estimated $IC_{50}$ of one micromolar and KB-7d cells were only about four-fold cross-resistant, in contrast to the cells marked resistance to etoposide. This type of improvement in activity against C-1-resistant cells has been reported for other C-4b-substituted epipodophyllotoxin derivatives in Y. Zhang and K. H. Lee, *Chin. Pharm. J.* 46:319 (1994). The relative growth inhibitory activities of 4b, like C-1, were similar for KB parent and -CPT100 cells and the KB-VIN20c sub-clone was about two-fold cross-resistant (Table 1). The unconjugated camptothecin analog, 3, inhibited KB cell growth with an estimated $IC_{50}$ value of 0.007 micromolar; it was equally active against the -7d subclone, and the -CPT100 cell lines was about 58-fold cross-resistant. The vincristine-resistant sub-line (-VIN20c) was marginally cross-resistant to 3, no more than 2-fold.

The relative inhibitory activities of compounds S-2 and 3 against the KB, -VIN20c and -7d cell lines were similar but the KB-CPT100 derivative was only six-fold cross-resistant to S-2. In fact, the conjugated inhibitor was marginally more active at inhibiting the growth of -CPT100 cells than compound 4b. Based on these findings, the growth inhibitory properties of compound S-2 closely resembles the behaviors of both the topoisomerase I- and topoisomerase II- inhibitory components.

EXAMPLE 11

Cell Toxicity of a Conjugated Inhibitor

Compounds 3, 4b, and S-2 were evaluated as cytotoxic agents and $LD_{50}$ values for a three-hour exposure were established. Results are reported in Table 2. Compound 4b was equipotent at killing all KB cell lines. The conjugated inhibitor more closely resembled the topoisomerase II-inhibitory component in that KB, -CPT100. and -VIN20c cells were killed by S-2 and 4b at equimolar doses. However, KB-7d cells appeared cross-resistant to the cytotoxic action of the conjugate, which more closely resembled the behavior of 3.

TABLE 2

Cytotoxicity Measured as Reduced Plating Efficiency

| | $IC_{50}$ ($\mu$M) | | |
|---|---|---|---|
| Cell Line | S-2 | 3 | 4b |
| KB | 4 (1, 7) | 10 (9, 11) | 3 (1.5, 4.5) |
| KB-7d | >15 | >16 | 5 (3.5, 6.5) |
| KB-CPT100 | 2 (1.1, 2.9) | | 2 (0.2, 3.8) |
| KB-VIN20c | 4.6 (2.6, 6.6) | 12 (16, 18) | 3 (1.5, 4.5) |

EXAMPLE 12

Stimulation of Intracellular Protein-DNA Complexes by a Conjugated Inhibitor

Figure 2A:
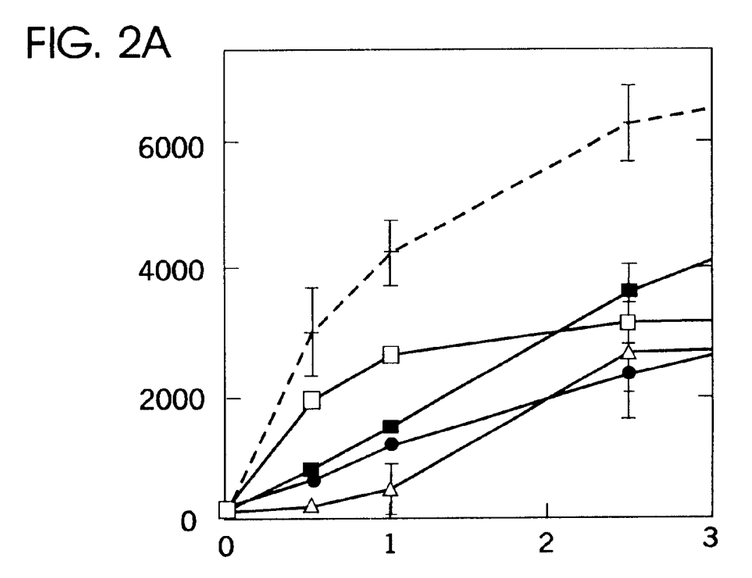
FIGS. 2A and 2B. Protein-associated DNA breaks in KB cells. Treatments were for one hour with test concentrations indicated on the ordinate. Etoposide C-1 (Δ); Compounds 3 (□), 4b (■), S-2 (●) and co-treatments with 3 and 4b (dotted line). Data obtained from triplicate treatments in a single experiment. Bars, SD. The effect of treatments at low concentration (0.5–2.5 μM) in 3A are results from 3B replotted for clarity.
Figure 2B:
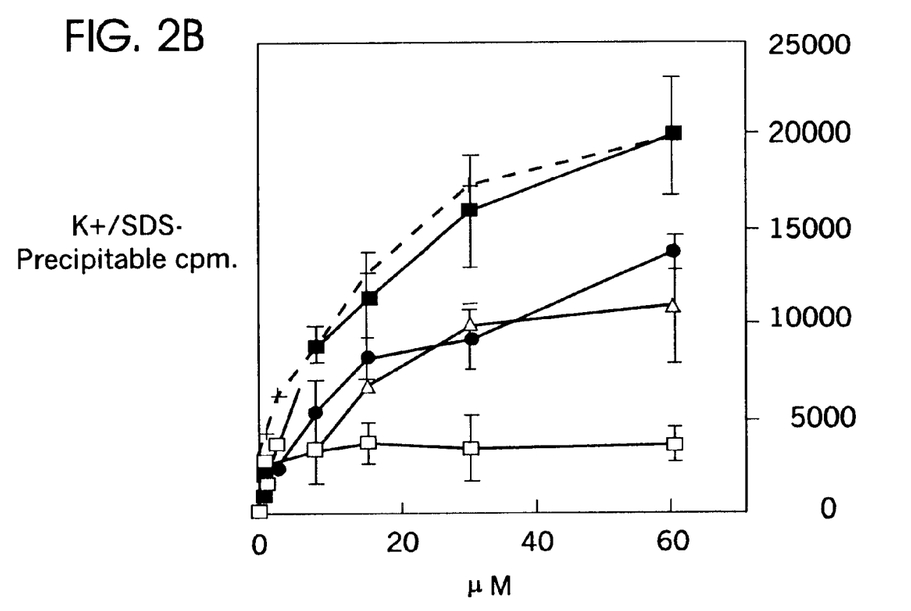
Figure 3:
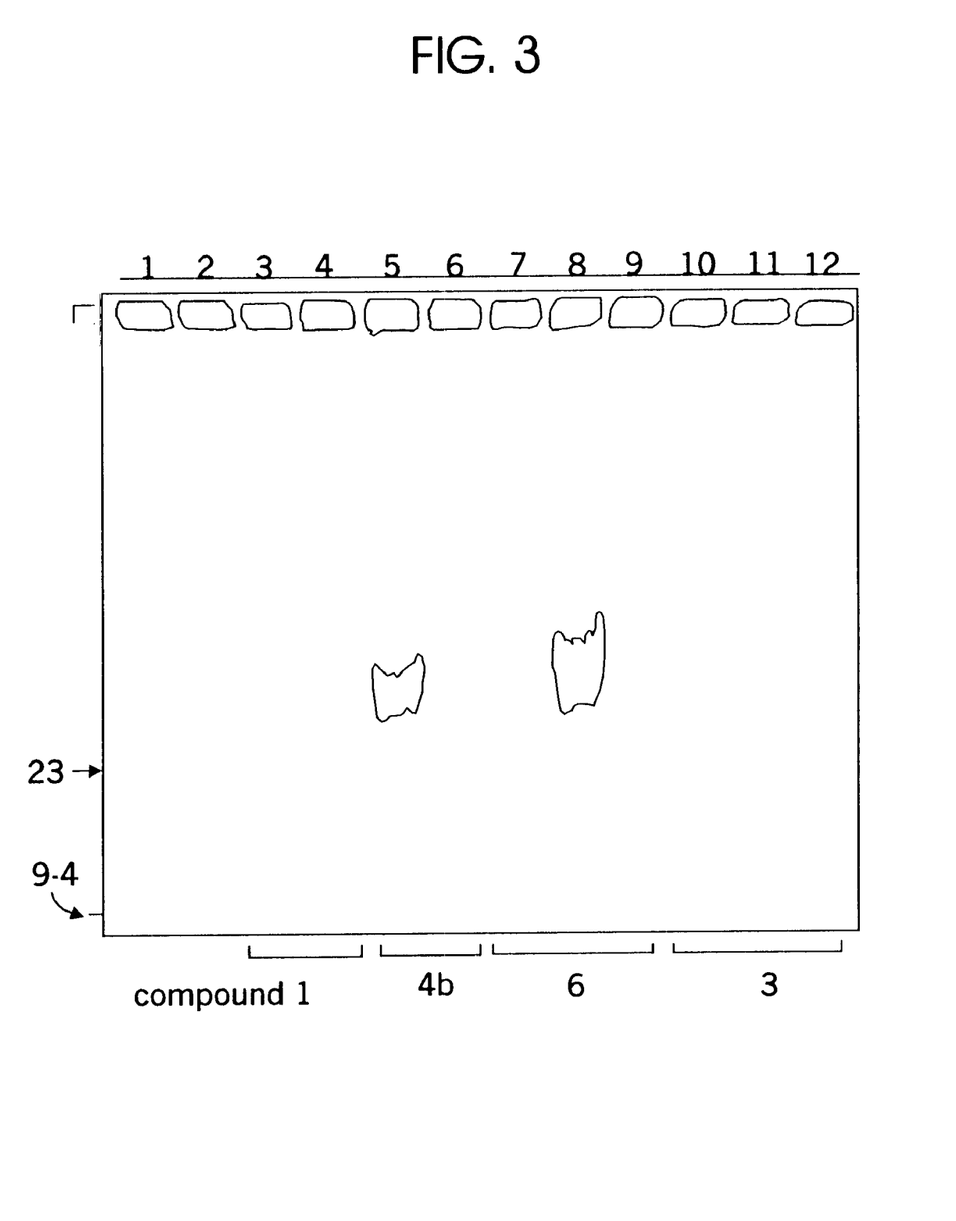

Intracellular activities of compounds 3, 4b and S-2 were compared to co-treatments with unconjugated inhibitors 3 and 4b using the potassium-SDS precipitation assay method. Etoposide (C-1) was included as the reference standard for 4b and S-2. Concentration-dependent protein-DNA complex formation in KB cells is shown in FIGS. 2A and 2B. Analysis of co-treated cultures showed that 3 and 4b gave additive effects at low test concentrations (0.5–2.5 micromolar, FIG. 2A) but at higher concentrations, co-treatment effects were indistinguishable from levels of protein-DNA complexes induced by 4b-treatment alone (FIG. 2B). At high test concentrations (7.5–60 micromolar), the intracellular activity of the conjugated derivative, S-2, was different from either 3 or 4b alone and in combination but was quite similar to the profile for C-1 (See, FIG. 2B). However, at concentrations of one micromolar and lower, the intracellular activity of S-2 and 4b were indistinguishable from other but different from C-1, which illicited no measurable response (See, FIG. 2A). Based on these comparisons, the relative intracellular activities of C-1, 4b and S-2 correlated well with the in vitro measurements except for one noticeable difference: the activities of 4b and S-2 in cells were clearly not dose-inhibitory at high concentration.

Further results show that S-2 was as effective as etoposide (C-1) in cleavage assays but was about ten-fold more active at inhibiting cell growth. To further characterize intracellular activities, compounds C-1, 3, 4b and S-6 were compared using a gel lysis assay method. Since this type of assay system is only sensitive enough to detect widespread double-stranded genomic breaks, the effect of topoisomerase II inhibitors like etoposide (C-1) will be readily observed whereas topoisomerase I inhibitors like camptothecin (C-2) will be marginally effective. Furthermore, genomic DNA integrity will generally be rapidly restored in cells upon drug-removal if the causitive lesions involve topoisomerases II- cleavable complexes. All compounds were evaluated at fifty-times the $IC_{50}$ concentration for KB cell growth inhibition and for 3 and S-2,- additional treatments at twenty-fold higher concentrations were examined. Results from a representative experiment are shown in FIG. 4. Control DNA's were intact and remained in the agarose plug at the gel origin (lanes 1 and 2). High molecular weight DNA fragments were detected after treatment with eight micromolar etoposide (lane 3) and the integrity of the DNA was restored intracellularly upon drug removal (lane 4), consistent with the known properties of etoposide-induced topoisomerase II cleavable-complexes. Resolution of similar DNA species using PFGE has shown the induced fragments to be 50 kbp and, under some circumstances 300 kbp. Fragmentation was also detected following treatment with four micromolar 4b (lane 5) and the lesions were reversible (lane 6), again consistent with the compounds known pharmacological action.

The camptothecin derivative, 3, was inactive at 0.4 micromolar (lane 10). At sixteen micromolar, marginal fragmentation was detected (compare lane 11 to the control in lane 1) which was not affected by reversing treatment (compare lane 12 to the control in lane 2). These effects of 3 are consistent with known actions of cleavable complex-forming topoisomerase I inhibitors. By comparison, marginal DNA fragmentation was detected for cells treated with the conjugated inhibitor S-2 at 0.8 micromolar (compare lanes 7 and 1) but at a twenty-fold elevated concentration, high molecular mass genomic fragments were detected (lane 8) and the integrity of the DNA was only partially restored following treatment reversal (compare lanes 8, 9 and 2). Based on these findings, intermediate levels of protein-DNA complexes were induced by compound S-2 relative to co-treatments with unconjugated components. At high concentrations, the majority of intracellular complexes induced by S-2 behaved as topoisomerase II-mediated DNA lesions.

The combined results of the experiments demonstrate that the topoisomerase I/topoisomerase II inhibitors of the present invention displayed lower activity in vitro relative to their unconjugated constituents, about two-fold at ten micromolar, but they retained target recognition specificity based on limited analysis of the activity profiles and induced cleavage products. Previous evaluation of semi-synthetic 4'-O—demethylepipodophyllotoxins with modifications at the C-4β- position revealed that bulky substituents are well tolerated. This same region corresponds to the "variable-substituent" domain in the composite pharmacophore model for topoisomerase II inhibitors proposed by MacDonald et al., *DNA Topoisomerase in Cancer* (Eds. Potmesil M, Kohn K W), pp 119–214, Oxford University Press, New York, (1991). It is also known that camptothecin analogs can bear C7-(aminoacylhydrazone)-formyl substituents without markedly affecting the ability to induce cleavable complexes. See, H. K. Wang et al., *Bioorg. & Med. Chem.* 2:1397 (1994).

In view of the current finding that conjugates bearing a substituent of substantial bulk also retained activity as topoisomerase I inhibitors, this suggests the interaction domain(s) within the presumed ternary complex is not proximal to the C7-position in camptothecin.

Evaluation of compounds 4b and S-2 as topoisomerase II inhibitors revealed that the stimulation of in vitro cleavable-complexes was dose-inhibitory for 4b and S-2 but not for etoposide, which is known to act saturably. Self-suppressive effects seen with cleavable complex-forming inhibitors, ascribed to unfavorable topoisomerase-drug-template interactions, have been reported for DNA intercalators acting both in vitro and in cellular assay systems. See, K. Tewey et al., *Science (Wash. DC)* 226:466 (1984) and A. Bodley et al., *Cancer Res.* 49:5969 (1989). As the induction of intracellular protein-associated DNA complexes by 4b and S-2 was clearly not dose inhibitory, the variant behavior observed seen in vitro is believed to be dependent upon enzyme and/or template interaction(s) which are peculiar to the in vitro assay conditions.

The experimental support presented for the dual target specificity of compound S-2 was based in part on measurements of cleavable complexes induced in vitro and in treated cells. Activity of the conjugated inhibitor relative to reference treatments was similar in the two assay systems and stimulatory effects of S-2 on cellular protein-DNA complexes were distinguishable from the response to co-treatment controls. These observations suggest that the conjugate remained intact under cell culture conditions, which is consistent with the reported stability of the imine linkage. Additional indirect support for intracellular topoisomerase I and II-targeting by S-2 came from growth inhibition and cytotoxicity studies, as a correlation was noted between these results and in vitro cleavage assay data when compounds S-2, 3 and 4b were compared.

EXAMPLE 13

In Vivo Effects of Compounds in Nude Mice with KB Cell Tumor Development

Three to six week old NCr nude mice (Taconic immunodeficient mice and rats) were inoculated subcutaneously in each flank with $2.5 \times 10^6$ cells, and tumors were allowed to grow. Treatment was started when the tumors were 250–500 mg as determined by caliper measurement and calculated according to the formula: tumor weight (mg)=(length (mm)× width (mm))/2. Drugs were given at the indicated doses on day 0 through 4, and tumor sizes were measured every several days. The tumor growth curves were generated as described previously. Toxicity was evaluated by changes in body weight.

Figure 4A:
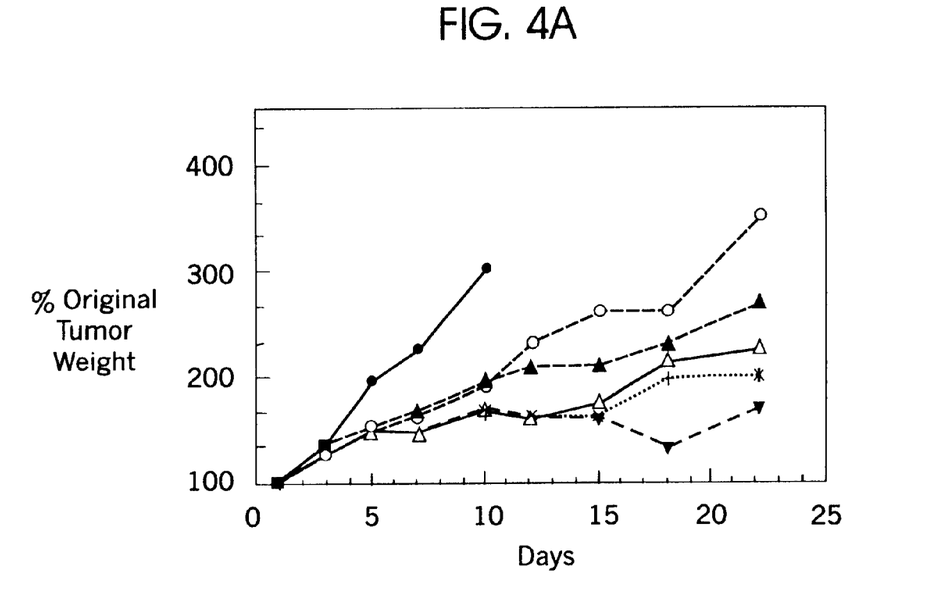
Figure 4B:
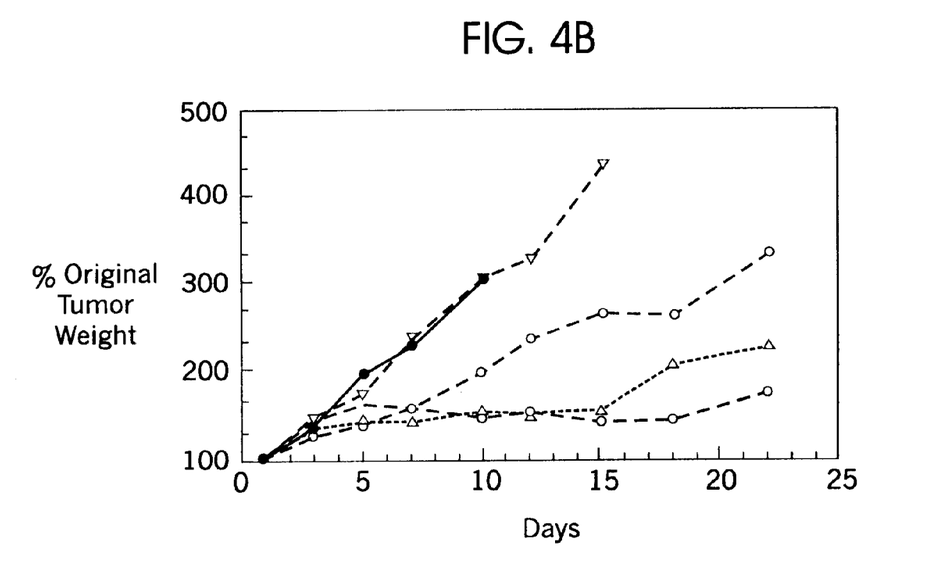

The results obtained in tests of compound S-1 are reported in FIG. 4A. The results obtained in tests of compound S-2 are reported in FIG. 4B.

The foregoing is illustrative of the present invention and is not to be construed as limiting thereof. The invention is defined by the following claims, with equivalents of the claims to be included therein.

That which is claimed is:

1. A compound having a structure according to formula I:

wherein:

$T_I$ is a camptothecin group;

$T_{II}$ is an epipodophyllotoxin, amsacrine, ellipticine, anthracycline antibiotic, or mitroxantrone group; and L is a linking group.

2. A compound according to claim 1, wherein $T_{II}$ is an epipodophyllotoxin group.

3. A compound according to claim 1, wherein $T_{II}$ is an amsacrine group.

4. A compound according claim 1, wherein $T_{II}$ is an ellipticine group.

5. A compound according to claim 1, wherein $T_{II}$ is an anthracycline antibiotic group.

6. A compound according to claim 1, wherein $T_{II}$ is a mitroxantrone group.

7. A compound according to claim 1 in a physiologically acceptable carrier.

8. A method of inhibiting topoisomerase I and topoisomerase II, said method comprising contacting topoisomerase I and topoisomerase II in vitro or in vivo with an inhibitory effective amount of a compound according to claim 1.

* * * * *

UNITED STATES PATENT AND TRADEMARK OFFICE
CERTIFICATE OF CORRECTION

PATENT NO.    : 6,420,377 B1
DATED         : July 16, 2002
INVENTOR(S)   : Lee et al.

It is certified that error appears in the above-identified patent and that said Letters Patent is hereby corrected as shown below:

<u>Title page,</u>
Item [56], References Cited, U.S. PATENT DOCUMENTS, delete Patent No. "4,197,246" and replace with the following:
-- 4,197,249 A  4/1980  Murdock et al……..260/380 --

Signed and Sealed this

Twenty-sixth Day of November, 2002

Attest:

JAMES E. ROGAN
Attesting Officer     Director of the United States Patent and Trademark Office